United States Patent [19]

Fujii

[11] Patent Number: 5,100,529

[45] Date of Patent: Mar. 31, 1992

[54] FLUORESCENCE DETECTION TYPE GEL ELECTROPHORESIS APPARATUS

[75] Inventor: Hidehiko Fujii, Kyoto, Japan

[73] Assignee: Shimadzu Corporation, Kyoto, Japan

[21] Appl. No.: 702,171

[22] Filed: May 20, 1991

[30] Foreign Application Priority Data

May 31, 1990 [JP] Japan .................................. 2-143797

[51] Int. Cl.[5] .......................... B01D 61/42; H01J 3/14; G01N 21/00
[52] U.S. Cl. .............................. 204/299 R; 250/234; 356/344; 364/413.01
[58] Field of Search ...................... 204/299 R, 182.8; 250/234; 356/344

[56] References Cited

U.S. PATENT DOCUMENTS

| | | | |
|---|---|---|---|
| 4,130,824 | 12/1978 | Amos et al. | 204/299 R |
| 4,675,095 | 6/1987 | Kambara | 204/299 R |
| 4,726,904 | 2/1988 | Ayers | 204/299 R |
| 4,811,218 | 3/1989 | Hunkapiller et al. | 204/299 R |
| 4,812,218 | 3/1989 | Hunkapiller et al. | 364/413.01 |
| 4,832,815 | 5/1989 | Kambara et al. | 204/299 R |
| 4,960,999 | 10/1990 | McKean | 204/299 R |
| 4,971,677 | 11/1990 | Kambara et al. | 204/299 R |

FOREIGN PATENT DOCUMENTS 0214713 3/1987 European Pat. Off. .
63-81256 4/1988 Japan .

OTHER PUBLICATIONS

European Search Report dated Oct. 4, 1991.

*Primary Examiner*—John Niebling
*Assistant Examiner*—Caroline Koestner
*Attorney, Agent, or Firm*—William L. Klima

[57] ABSTRACT

With respect to a gel which is mounted on a gel electrophoresis apparatus, a calibration process is provided before starting of measurement to obtain calibration data for bringing a portion of the gel irradiated with excitation light onto the optical axis of a light receiving optical system for each scanning point, to perform measurement while controlling relative positional relation between the optical path of the excitation light and the optical axis of the light receiving optical system through the calibration data. Displacement, which may be inevitably caused between the optical axis of the light receiving optical system and the position irradiated with the excitation light by errors in working, assembling and adjustment, is basically eliminated, and sensitiveness irregularity is also removed.

11 Claims, 9 Drawing Sheets

FLUORESCENCE DETECTION TYPE GEL ELECTROPHORESIS APPARATUS

BACKGROUND OF THE INVENTION

1. Field of the Invention

The present invention relates to an apparatus for DNA sequencing or the like, and more particularly, it relates to a gel electrophoresis apparatus for gelelectrophoresing fluorescence-labelled samples and scanning optical systems for exciting and receiving fluorescence in a direction perpendicular to the electrophoresis direction, thereby detecting the electrophoresis pattern.

2. Description of the Background Art

Fluorescence-labelled samples are DNA fragments which are fluorescence-labelled in a primer part or a dideoxy part and prepared by the Sanger's sequencing method. A developed pattern obtained by gel-electrophoresing the fluorescence-labelled samples directly provides the DNA sequence.

Figure 11:
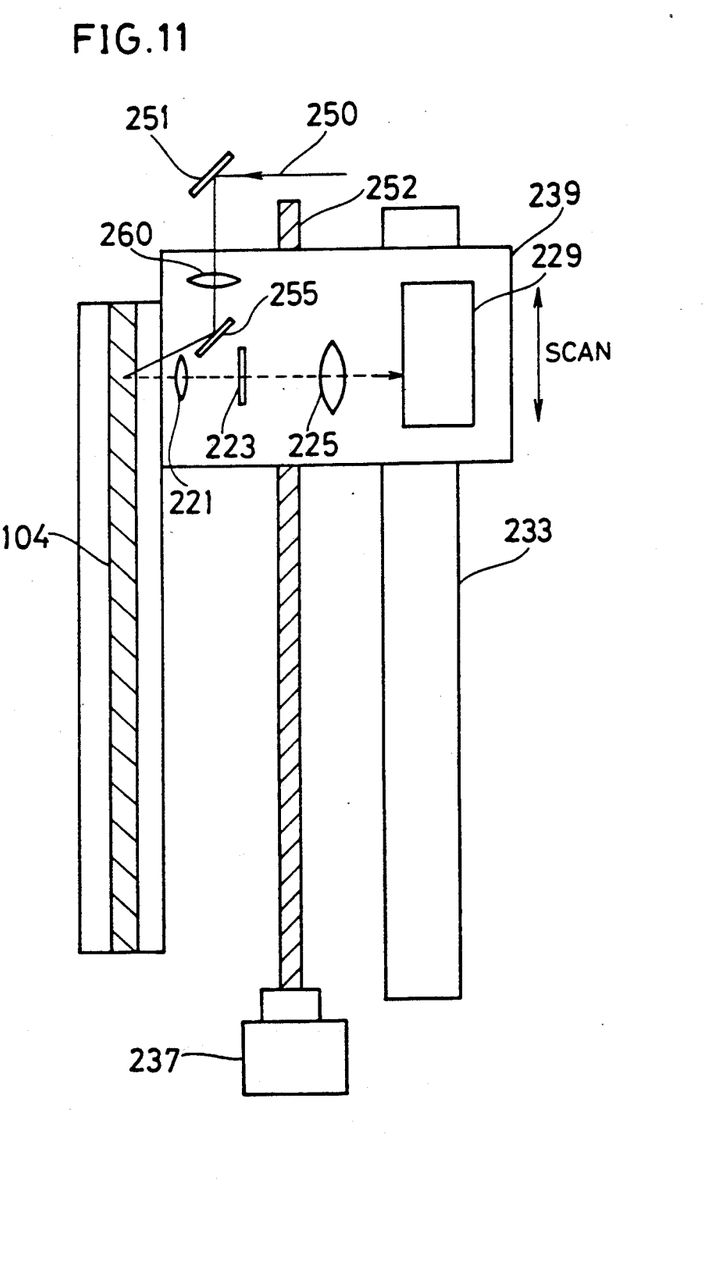
FIG. 11 is a schematic plan view showing a conventional gel electrophoresis apparatus.

FIG. 11 shows a fluorescence detection type gel electrophoresis apparatus, which is described in U.S. Pat. No. 4,811,218. Fluorescence-labelled samples are electrophoresed in an electrophoresis gel 104, which is held between glass panels to extend perpendicularly to the figure plane, along the said perpendicular direction. A stage 239 is guided by a guide rail 233, and scanned in a direction perpendicular to the electrophoresis direction, i.e., vertically in this figure, by rotation of a screw 252 which is driven by a motor 237. The stage 239 is provided with a condenser lens 260, so that a laser beam 250, which is excitation light, is reflected by a mirror 251 to enter the lens 260, and further reflected by another mirror 255 provided on the stage 239, to irradiate a portion of the electrophoresis gel 140 to be measured. Fluorescence outgoing from the measured portion is collected by a condenser lens 221 provided on the stage 239, selected by an interference filter 223 to pass through a lens 225, and detected by a photomultiplier tube 229.

In the apparatus shown in FIG. 11, the electrophoresis gel 104, the scanning direction, which is determined by the screw 252 and the guide rail 233, and the direction of incidence of the excitation light upon the condenser lens 260 must be absolutely parallel to each other. This condition must be regularly satisfied also when the gel 104 is exchanged.

Figure 12:
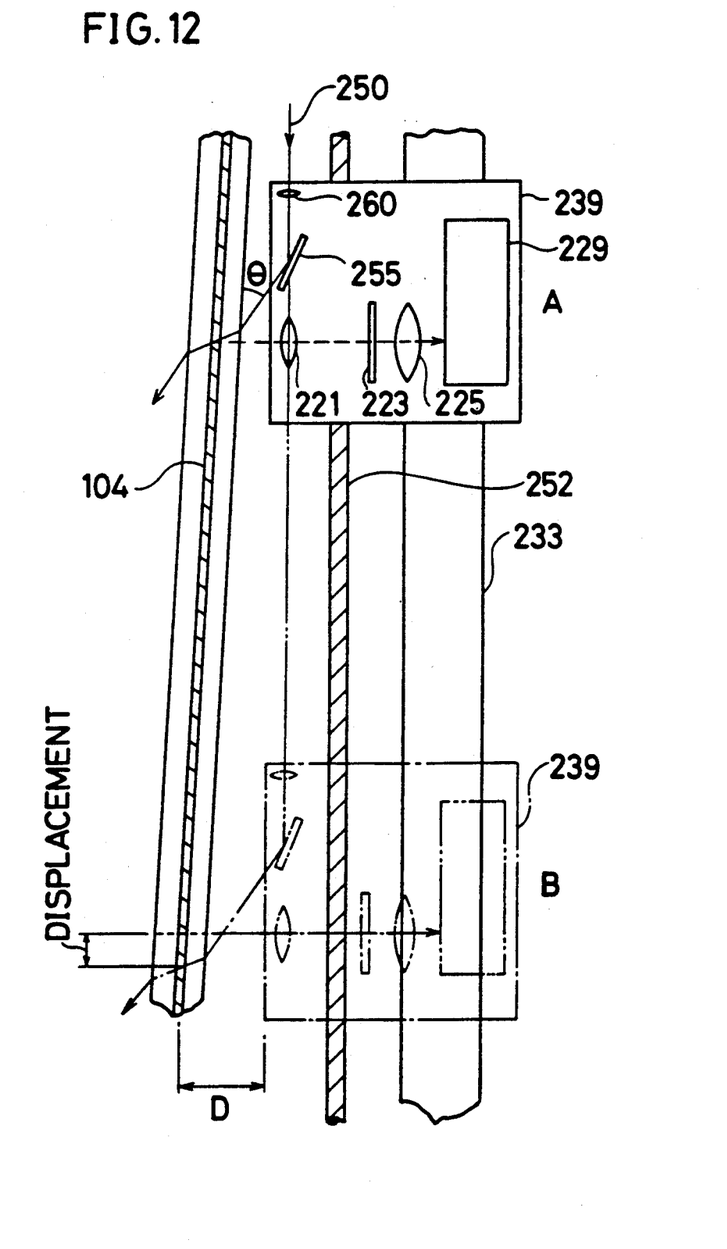
FIG. 12 is a plan view of an essential part showing a problem of the apparatus shown in FIG. 11.

FIG. 12 shows such a case that the above condition is not satisfied. In a certain scanned position A, the gel portion irradiated with the excitation light 250 is correctly located on the optical axis of the light receiving optical system, to provide a strong signal. However, if the glass panels holding the gel 104 are varied in thickness, or the gel 104 is not sufficiently parallel with the screw 252, for example, the gel portion irradiated with the excitation light 250 is displaced from the optical axis of the light receiving optical system in another scanned position B as shown in FIG. 12, whereby the signal strength is so reduced that no signal is detected in an extreme case. Thus, the signal strength is varied with the position.

The lens 225 is adapted to reduce such displacement. In this optical system, however, an angle $\theta$ of incidence is set at a small value of about 20° to 35° in order to reduce scattered light. Therefore, it is impossible to sufficiently compensate for the displacement between the excited position of the gel 104 and the optical axis of the light receiving optical system caused by variation of a distance D between the gel 104 and the stage 239 due to ununiformity of thickness of the glass panels or an error in parallelism.

In order to eliminate such displacement, it is conceivable to detect a spot position of the excitation light and move the optical axis by a negative-feedback servo mechanism. However, such a method inevitably requires a detector for the spot position, and hence the structure is complicated.

SUMMARY OF THE INVENTION

An object of the present invention is to provide a gel electrophoresis apparatus for detecting an electrophoresis pattern while scanning light excitation and receiving optical systems in a direction perpendicular to an electrophoresis direction, which can correctly detect fluorescence even if a gel, a scanning direction and a direction of incidence of excitation light on a scanning stage are not strictly parallel to each other, with no position detector for an excitation light spot.

The present invention is described with reference to FIG. 1.

A scanning control part 46 is provided in order to control a scanning mechanism 44 for scanning light excitation and receiving optical systems. Numeral 30 denotes a scanning position detection part for detecting a scanning position by outputs from the scanning mechanism 44 and the scanning control part 46, while receiving scattered light from a portion of a gel irradiated with excitation light for detecting the scanning position. Numeral 32 denotes moving means for changing relative positional relation between the optical path of the excitation light and the optical axis of the light receiving optical system. Numeral 34 denotes signal detection means which is provided with an optical system and a photo detector part for detecting the scattered light and fluorescence from the position of the gel irradiated with the excitation light. Numeral 36 denotes a calibration part, which drives the moving means 32 in several scanning positions within a scanned region of calibration scanning before introduction of samples or before samples reach a measuring part after introduction of the samples after the gel employed for measurement is mounted, to obtain calibration data related to the amount of movement of the moving means 32 attained when a portion of the gel irradiated with the excitation light comes onto the optical axis of the light receiving system on the basis of a signal from the signal detection means 34 and store the same in a storage part 38 with scanning position data. The storage part 38 is adapted to store the calibration data with the scanning position data. Numeral 40 denotes a moving means control part which reads the calibration data corresponding to the scanning position from the storage part 38 in measurement, to set the amount of movement of the moving means 32 for each scanning position. In measurement, a detection signal (actual signal) by the signal detection means 34 is incorporated in and processed by a signal processing part 42.

Figure 6:
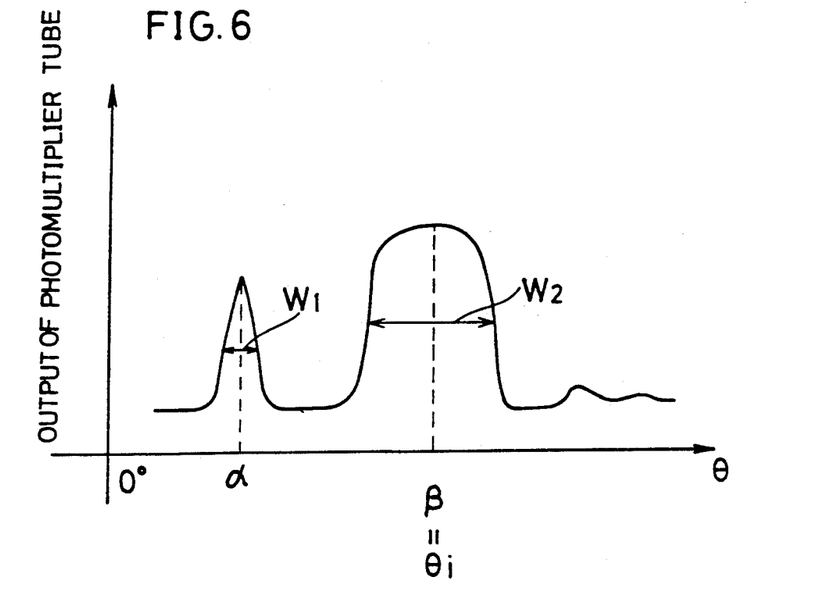
FIG. 6 is a waveform diagram showing an output of a photomultiplier tube in calibration.
Figure 7:
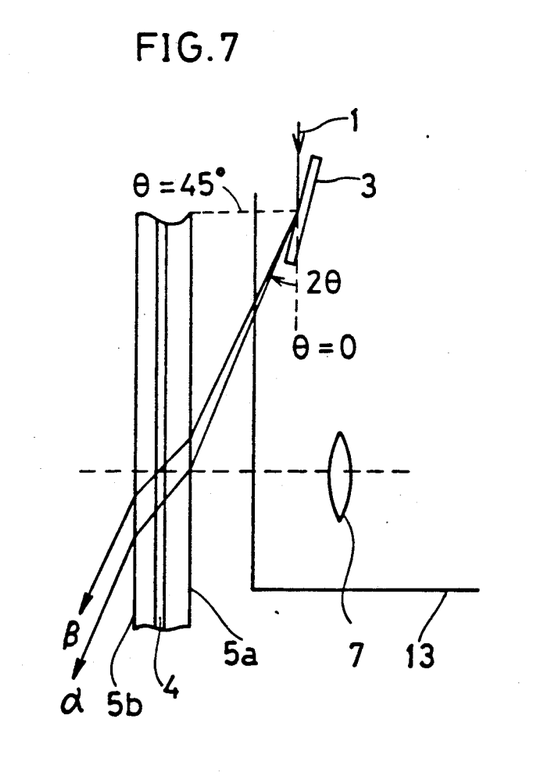
FIG. 7 is a schematic plan view showing change of an optical path of excitation light caused by rotation of a galvano mirror.

Referring to FIG. 7, a gel 4 employed for measurement is mounted and a moving stage 13 carrying light excitation and receiving optical systems is stopped at a point within a scanned region before electrophoresed samples reach a measuring point. Then the optical path of excitation light or the optical axis of the light receiving optical system is moved so that the intersection point between the optical axis of the light receiving optical system and the optical path of the excitation light is moved from the outer side of a glass panel 5a, which is provided on an excitation light source side, to the outer side of another glass panel 5b, which is provided on an opposite side, through the inner side of the glass panel 5a, the gel 4, and the inner side of the glass panel 5b, and an output of the light receiving optical system (spectroscopic means for measuring fluorescence may be removed) is taken with respect to such movement. FIG. 6 shows its output plot. The first peak (angle α of incidence) is caused by scattering of the excitation light on the surface of the glass panel 5a, and has a narrow width. The next peak (angle β of incidence) is caused by scattering on the gel 4 or fluorescence, and at this peak, the position of the gel 4 irradiated with the excitation light is correctly located on the optical axis of the light receiving optical system. At this time, numerical values, such as a voltage and a current corresponding to the amount of movement, supplied to the moving means 32 are regarded as calibration data at this scanning point.

The above operation is performed in a number of points within the scanned region before the electrophoresed samples reach the measuring point, to store calibration data supplied to the moving means 32 with respect to the respective scanning points are tabled and stored in the storage part 38.

In order to perform measurement with a pitch narrower than that at the scanning points where the calibration data are measured, calibration data in another measuring point may be calculated on the basis of the measured calibration data by interpolation, to store the same in the storage part 38.

Ordinary scanning is started slightly before the electrophoresed samples reach the measuring point, to start measurement. At this time, the moving means control part 40 controls the moving means 32 in accordance with the calibration data called from the storage part 38 at each point of scanning in synchronization with the scanning, to change the optical path of the excitation light or the optical axis of the light receiving optical system. Since the calibration data are so produced that the positions of the gel 4 irradiated with the excitation light come onto the optical axis of the light receiving optical system in the respective points of scanning or calculated on the basis thereof, it is possible to satisfy such a condition that the positions of the gel 4 irradiated with the excitation light regularly come onto the optical axis of the light receiving optical system during scanning for measurement, thereby preventing displacement.

According to the present invention, a calibration process is provided for a gel which is mounted on a gel electrophoresis apparatus before measurement is started to obtain calibration data for bringing portions of the gel irradiated with excitation light onto an optical axis of a light receiving system for respective scanning points, and measurement is performed while controlling relative positional relation between the optical path of the excitation light and the optical axis of the light receiving optical system through the calibration data, whereby it is possible to basically prevent displacement between the optical axis of the light receiving system and positions irradiated with the excitation light, which can inevitably be caused by errors in working, assembling and adjustment, and sensitiveness irregularity is also removed. Further, glass panels for holding the gel can be exchanged with no inconvenience. Therefore, absolutely no problem is caused in performance even if errors are caused in working, assembling or adjustment. Thus, it is easy to perform working, assembling and adjustment, to reduce the apparatus cost.

These and other objects, features, aspects and advantages of the present invention will become more apparent from the following detailed description of the present invention when taken in conjunction with the accompanying drawings.

DESCRIPTION OF THE PREFERRED EMBODIMENTS

Figure 2:
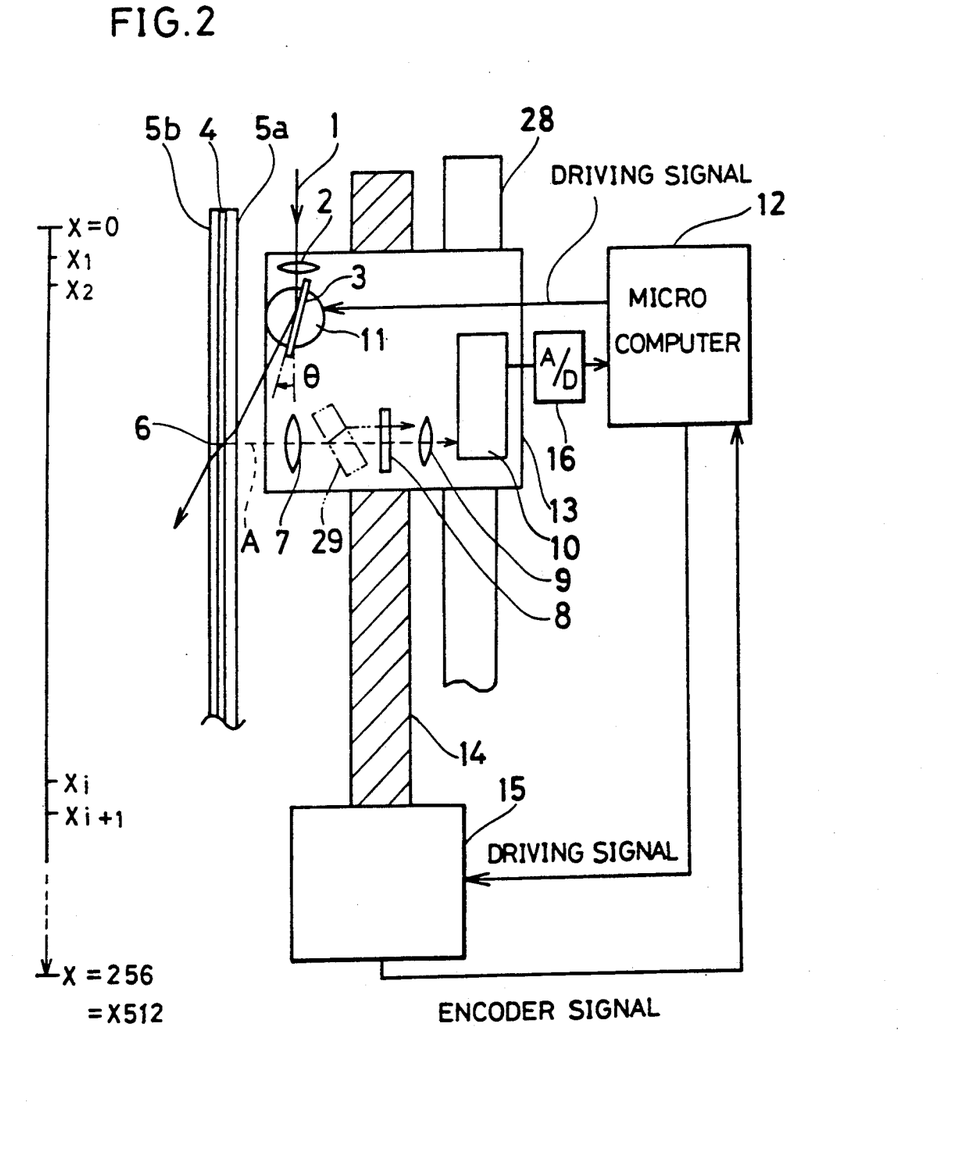
FIG. 2 is a schematic plan view showing an embodiment of the present invention.

FIG. 2 illustrates an embodiment of the present invention.

Numeral 4 denotes an electrophoresis gel of 6% polyacrylamide, for example, which is held between glass panels 5a and 5b of Pyrex having thickness of 5 mm, for example. This gel 4 is formed in thickness of 0.35 mm, for example, and raised perpendicularly to the figure plane. Fluorescence-labelled samples are electrophoresed in the electrophoresis gel 4 perpendicularly to the figure plane. These samples are labelled with a fluorescent material FITC, for example, and excited by an $Ar^+$ laser of 488 nm, to emit fluorescence of 520 nm.

A moving stage 13 is guided by a guide rail 28 such as a cross roller or a dovetail groove, and driven by rotation of a screw 14 which is driven by a scanning motor 15, to be scanned in a direction perpendicular to the electrophoresis direction. A condenser lens 2 is provided on the stage 13 for receiving an $Ar^+$ laser beam 1, which is excitation light. This excitation light beam 1 is incident in parallel with the electrophoresis gel 4 and the scanning direction of the stage 13, to be collected by the lens 2. A mirror 3 is provided on the stage 13 in order to introduce the excitation light beam 1, which is collected by the lens 2, into the electrophoresis gel 4. The angle of rotation of the mirror 3 can be changed by a galvano scanner 11 (G120D by General Scanning Inc., U.S.A., for example). Such an angle of rotation of the mirror 3 is controlled by a current which is fed to the galvano scanner 11. An excitation optical system and a light receiving optical system are set so that the laser beam 1 is incident upon the gel 4 at an angle of about 20° to 35°, in order to reduce scattered light entering the light receiving optical system.

In order to collect and detect light from a position 6 of the electrophoresis gel 4 irradiated with the excitation light beam 1, the stage 13 is provided thereon with an objective lens 7, and a condenser lens 9 for collecting the light collected by the objective lens 7 through an interference filter 8 of 520 nm. Further, a photomultiplier tube 10 is provided in order to detect fluorescence collected by the condenser lens 9. The condenser lens 9 is adapted to reduce a parallel and wide luminous flux, which passes through the interference filter 8, into the size of the photoelectric surface of the photomultiplier tube 10. This lens 9 may be omitted if the photomultiplier tube 10 has a wide photoelectric surface.

Numeral 16 denotes an A-D converter, which converts a signal detected by the photomultiplier tube 10 to a digital signal and incorporates the same in a microcomputer 12.

The angle of rotation of the mirror 3 is controlled by the galvano scanner 11 through a driving signal supplied from the microcomputer 12.

The moving stage 13 is scanned by rotation of the screw 14, which is driven by a scanning motor 15. This scanning motor 15 is provided with an encoder, so that information for a scanned position of the stage 13 is incorporated from the encoder in the microcomputer 12.

Figure 1:
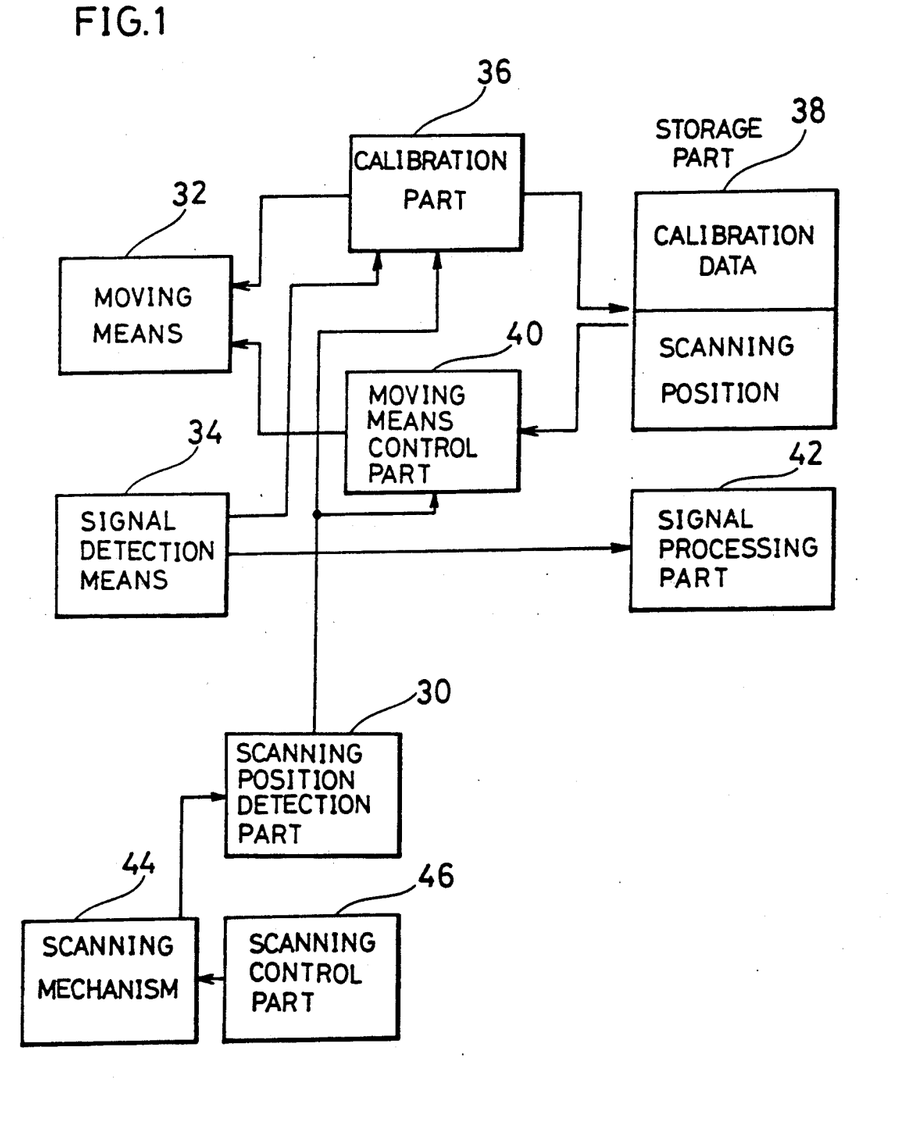
FIG. 1 is a block diagram showing the present invention.

Referring to FIGS. 1 and 2, the moving means 32 corresponds to the mirror 3 and the galvano scanner 11, the scanning mechanism 44 corresponds to the screw 14 and the scanning motor 15, and the signal detection means 34 corresponds to the photomultiplier tube 10, while the scanning position detection part 30, the calibration part 36, the storage part 38, the moving means control part 40, the signal processing part 42 and the scanning control part 46 are implemented by the microcomputer 12.

For the following description of an exemplary operation, it is assumed that a scanned region is 256 mm in total and a portion expressed by coordinates of X=0 to 256 is scanned from the top to the bottom, while the optical axis A of the light receiving optical system is moved in the range of X=0 to 256 in FIG. 2. Assuming that signals are incorporated in 512 positions (measuring points), a fluorescence signal is incorporated in the microcomputer 12 every movement of X by 0.5 mm.

X coordinates of signal incorporating points are set as $X_i$ (i = 1, 2, ... 512), and every four signal incorporating points ($X_4$, $X_8$, $X_{12}$, ... $X_{512}$) are assumed to be the points where the optical axis of the excitation light is so moved to measure calibration data that the position 6 irradiated with the excitation light comes onto the optical axis A of the light receiving optical system.

The operation of the embodiment is now described with reference to flow charts shown in FIGS. 3, 4 and 5, and FIGS. 6 and 7.

An operator mounts the gel 4, and introduces samples to start the electrophoresis.

Figure 3:
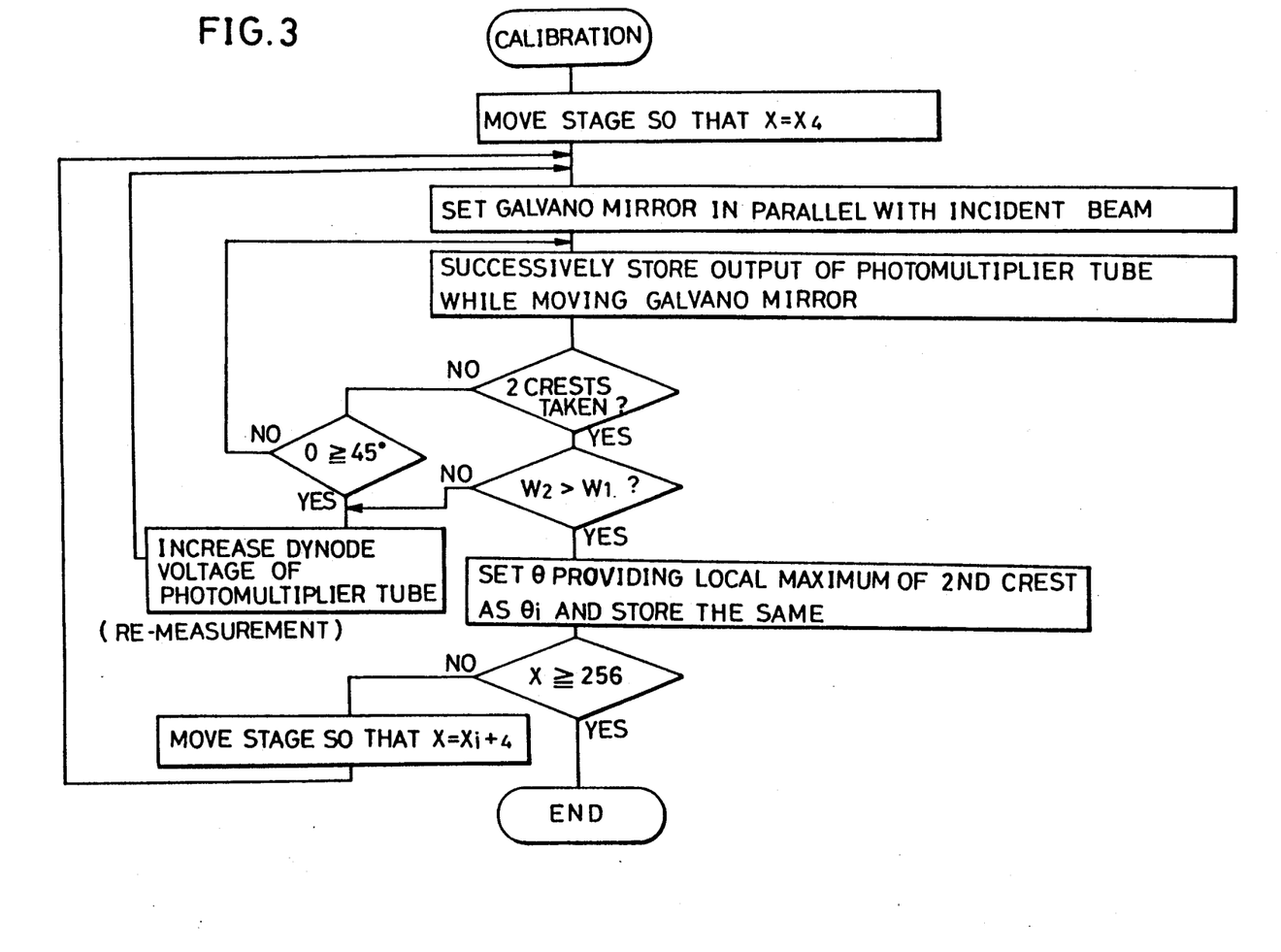
FIG. 3 is a flow chart showing a calibration process in the operation of the embodiment.

FIG. 3 shows a calibration process for finding such an angle $\theta_i$ of rotation of the galvano mirror 3 that the position irradiated with the excitation light comes onto the optical axis of the light receiving system with respect to the X-coordinates $X_4$, $X_8$, ... $X_{512}$.

First, the angle $\theta$ of the galvano mirror 3 is brought into parallel with the direction of incidence of the excitation light beam 1 ($\theta=0$). Then, the mirror 3 is rotated until the angle $\theta$ reaches 45°, i.e., an angle at which the excitation light beam 1 is perpendicularly incident upon the gel 4, to take an output of the photomultiplier tube 10 at this time. This output is plotted as shown in FIG. 6. At the first peak ($\theta=\alpha$) shown in FIG. 6, a point where the excitation light is scattered on the surface of the glass panel 5a comes onto the optical axis of the light receiving optical system. At the next peak ($\theta=\beta$), the portion of the gel 4 irradiated with the excitation light beam 1 just comes onto the optical axis of the light receiving optical system (see FIG. 7). The peak of the position $\beta$ is wider than that of the position $\alpha$. This is because the gel 4 has thickness, and the excitation light beam 1 is incident at an angle approximately parallel to the gel 4. While most of the photomultiplier tube output shown in FIG. 6 is scattering of the excitation light and its wavelength is that of the excitation light, this light is extremely strong and it is possible to sufficiently obtain a signal without particularly removing the interference filter 8 for fluorescence. However, the interference filter 8 may be removed. Further, various peaks obtained when $\theta$ is increased in excess of $\beta$ are caused by multiple reflection of the excitation light beam 1 in the glass panels 5a and 5b with no regard in this case. Therefore, if the second crest has a wider half-width (or 1/e width etc.) than the first crest, $\theta$ providing the local maximum of the second crest is set as $\theta_i$, and stored with the scanning positions $X_i$. Thereafter the moving table is moved and the same calibration operation is performed at points of X(i+4), X(i +8), ... up to $X_{512}$. Thus determined are calibration data $\theta_4$, $\theta_8$, ... $\theta_{512}$.

Figure 4:
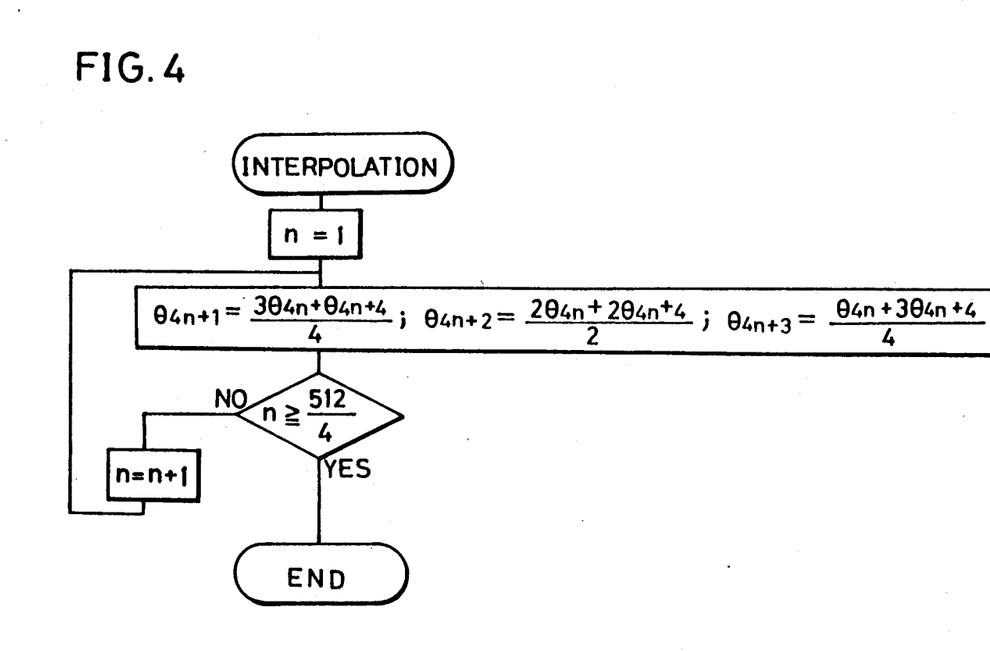
FIG. 4 is a flow chart showing an interpolation process.

FIG. 4 shows an interpolation process for obtaining calibration data of scanning positions, which are not yet determined in the calibration process shown in FIG. 3, by interpolation. Although FIG. 4 shows linear interpolation, such interpolation may alternatively be performed with an appropriate curve.

Figure 5:
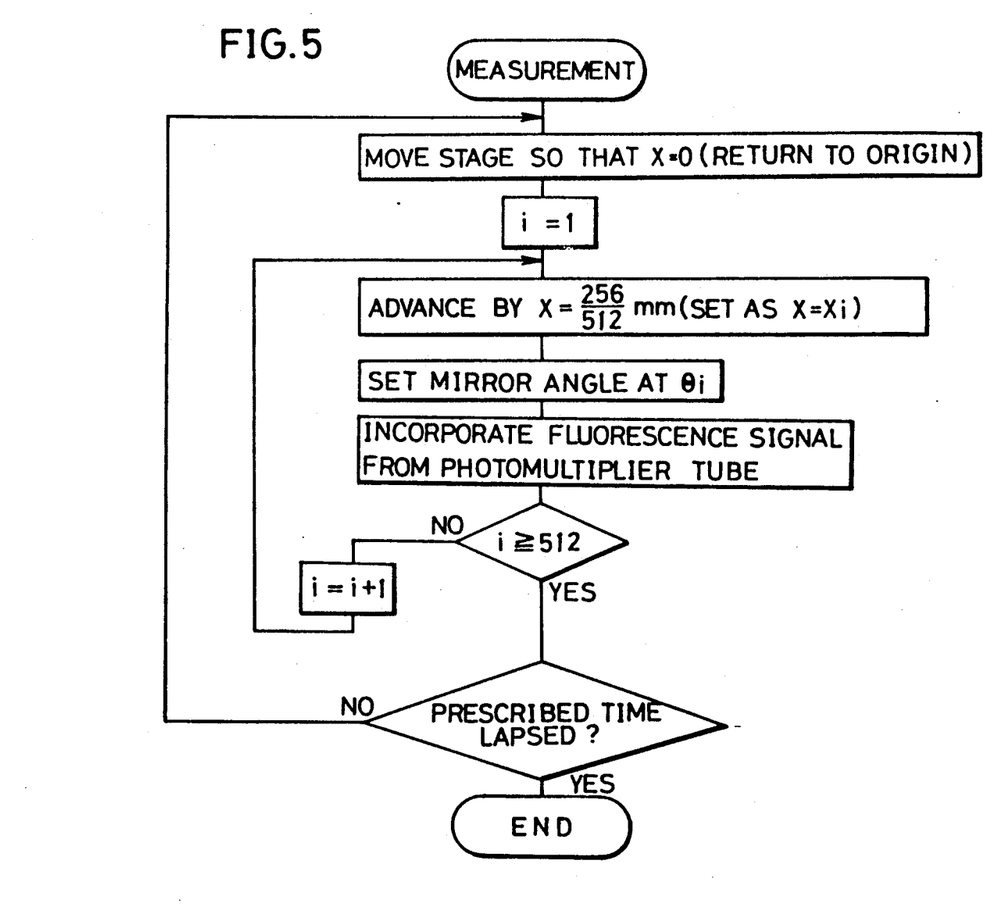
FIG. 5 is a flow chart showing a measurement process.

FIG. 5 shows a measurement process.

The stage 13 is successively moved to measuring points, and the mirror 3 is set at angles of the calibration data obtained in the calibration process and the interpolation process, to incorporate signals. Since the mirror 3 and the stage 13 have inertia in practice, the stage 13 is not stopped at every measuring point but scanning is continuously performed to set the angles of the mirror 3 in synchronization therewith.

Figure 8:
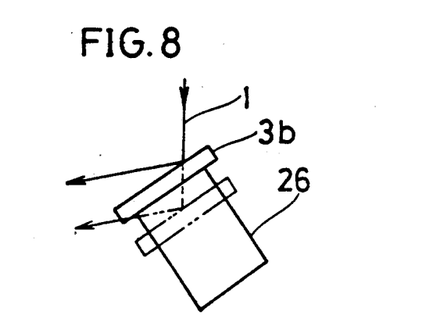
FIGS. 8 and 9 are schematic plan views showing other exemplary means for moving optical paths of excitation light.

FIG. 8 shows a mirror 3b, employed in place of the rotary mirror 3 shown in FIG. 2, which is mounted on a piezoelectric element 26. A voltage is supplied to the piezoelectric element 26 to move the mirror 3b in parallel, thereby moving an optical path of excitation light. Such a piezoelectric element 26 may be implemented by a LAN series product by Tokin Co., Ltd., Tokyo, Japan, for example.

Figure 9:
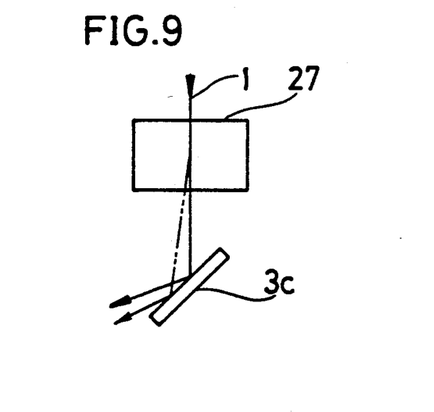

FIG. 9 shows another exemplary means for moving an optical path of excitation light. A mirror 3c is fixed so that an excitation light beam 1 is incident upon the mirror 3c through an acoustic optical element 27. The optical path of the excitation light incident upon a gel 4 is varied with a voltage which is applied to the acoustic optical element 27.

Figure 10:
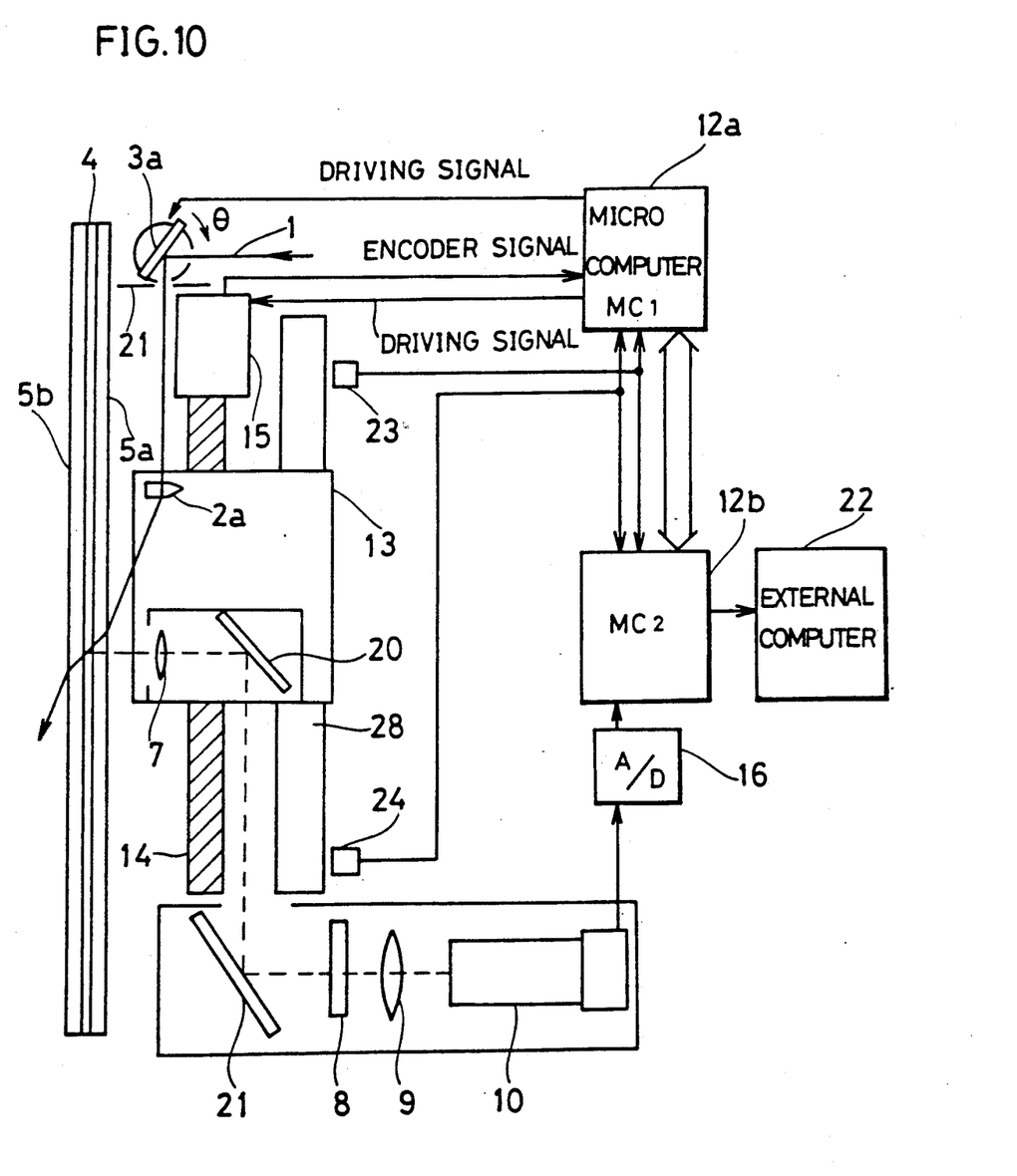
FIG. 10 is a schematic plan view showing another embodiment of the present invention.

FIG. 10 shows another embodiment of the present invention.

The embodiment shown in FIG. 10 is different from that of FIG. 2 in that a photoelectric conversion part as well as a mirror 3a for changing the direction of the optical path of excitation light are in the exterior of a moving stage 13, and in that a scanning and control microcomputer 12a for scanning and setting mirror angles is provided independently of a microcomputer 12b for signal incorporation.

An excitation light beam 1 is reflected by the galvano mirror 3a and passes through a mask 21, to be incident upon the stage 13. The stage 13 is provided thereon with a lens 2a in the form of a partially cut convex lens, and the excitation light beam 1 is deflected by this lens 2a to illuminate a gel 4. The focal point of the convex lens 2a is substantially at the intersection point between the optical axis of the light receiving optical system and the gel 4. The lens 2a may alternatively be implemented by an ordinary convex lens which is combined with a mirror, or a convex lens which is combined with a wedge prism.

The stage 13 is provided thereon with an objective lens 7 for incorporating light from the gel 4 or glass panels 5a and 5b, and a mirror 20 for guiding the light, which is converted to parallel light by the objective lens 7, to the exterior of the stage 13. In the exterior of the stage 13, there are provided a mirror 21 for changing the direction of the parallel light guided from the mirror 20, an interference filter 8 for fluorescence, a condenser lens 9, and a photomultiplier tube 10 for photoelectrically converting fluorescence which is condensed in a proper size by the condenser lens 9. Numeral 16 denotes an A-D converter, and a signal incorporated in the microcomputer 12b through the A-D converter 16 is guided to an external computer 22, to be subjected to data processing for DNA sequencing.

The scanning and control microcomputer 12a supplies a required driving signal for a scanning motor 15. Sensors 23 and 24 are provided on both ends of a scanned region. Signals from these sensors 23 and 24 are incorporated in the microcomputer 12a, so that the driving direction is changed by the driving signal at the end portions of the scanned region. The scanning motor 15 is provided with an encoder, so that an encoder signal is fed back to the microcomputer 12a to maintain the motor 15 at a constant speed of rotation.

The microcomputer 12b is devoted to control of the A-D converter 16, which incorporates the signal from the photomultiplier tube 10. In this case, clocks of the A-D converter 16 are not particularly synchronous with those of the scanning moter 15, but outputs of the sensors 23 and 24 are merely supplied to the microcomputer 12b as signals indicating start and end of scanning. Such a structure causes no inconvenience in practice, and the program is extremely simplified by providing the microcomputers 12a and 12b independently of each other.

Flow charts showing the operation of the embodiment shown in FIG. 10 are substantially identical to those shown in FIGS. 3, 4 and 5. The difference resides in the point that, although the angle (stroke) for rotating the galvano mirror in FIG. 10 may be smaller than that in FIG. 2, the angle of rotation must be higher in accuracy. While the microcomputers 12a and 12b simultaneously act, calculate and store in the calibration process shown in FIG. 3 and the interpolation process shown in FIG. 4, the microcomputers 12a and 12b act absolutely independently of each other in the measurement process shown in FIG. 5. Values of the calibration data $\theta_i$ determined in FIGS. 3 and 4 are stored in a memory of the microcomputer 12a with the scanning positions $X_i$, to change the angle $\theta$ of the galvano mirror 3 in synchronization with scanning under control by the microcomputer 12a. In parallel with this, the microcomputer 12b incorporates the signal output from the photomultiplier tube 10, and transmits the same to the external computer 22 to obtain the electrophoresis pattern.

The embodiment shown in FIG. 10 is superior to that shown in FIG. 2 in a point that the weight of the stage 13 can be reduced with a smaller number of elements, and in a point that the program is simplified by independent provision of the microcomputers.

Although each of the aforementioned embodiments shows moving means for changing the optical path of the excitation light in order to change relative positional relation between the optical path of the excitation light and the optical axis of the light receiving optical system, the optical path of the excitation light may alternatively be fixed so that the optical axis of the light receiving optical system is moved. In this case, the moving table may be moved in the scanning direction at the scanned points, or a glass block 29 may be arranged on the optical axis of the light receiving optical system as shown by chain lines in FIG. 2, to rotate the same.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A fluorescence detection type gel electrophoresis apparatus for gel-electrophoresing fluorescence-labelled samples and scanning excitation and light receiving optical systems for fluorescence in a direction perpendicular to the electrophoresis direction with a scanning mechanism thereby detecting the electrophoresis pattern, said apparatus comprising:

a scanning position detection part for detecting scanning positions of said excitation and light receiving optical systems;

moving means for changing relative positional relation between the optical path of excitation light and the optical axis of said light receiving system;

a calibration part for performing calibration scanning before introduction of samples or before said samples reach a measuring part after introduction of said samples after a gel employed for measurement is mounted, driving said moving means in some scanning positions within a scanned region in said calibration scanning and obtaining calibration data related to amounts of movement of said moving means at the time when portions of said gel irradiated with said excitation light come onto the optical axis of said light receiving optical system on the basis of signals from signal detection means for storing the same in a storage part with scanning position data;

a storage part for storing said calibration data with said scanning position data; and a moving means control part for reading calibration data corresponding to scanning positions from said storage part in measurement for setting an amount of movement of said moving means for every scanning position.

2. A fluorescence detection type gel electrophoresis apparatus in accordance with claim 1, wherein said calibration part regards data, being related to an amount of movement providing the local maximum of a second crest being significantly wider than a first crest among local maximums of outputs from a photoelectric converter provided on the optical axis of said light receiving optical system with respect to successive movement of the optical path of said excitation light or the optical axis of said light receiving optical system in such a direction that the intersection point between the optical axis of said light receiving system and the optical path of said excitation light comes to the outer side of a glass panel, supporting said gel, being opposite to an excitation light source from such a state that the intersection point is on the outer side of another glass panel being closer to said excitation light source, as said calibration data.

3. A fluorescence detection type gel electrophoresis apparatus in accordance with claim 1, wherein calibration data of measuring points other than scanning points used for obtaining calibration data are calculated through interpolation on the basis of said measured calibration data, so that said calculated calibration data are also stored in said storage part with said measured calibration data.

4. A fluorescence detection type gel electrophoresis apparatus in accordance with claim 1, wherein said scanning mechanism includes a moving stage carrying said moving means and a photoelectric conversion part of said light receiving optical system.

5. A fluorescence detection type gel electrophoresis apparatus in accordance with claim 1, wherein said scanning mechanism includes a moving stage, and a photoelectric conversion part of said light receiving optical system is separated from said moving stage, while said moving stage is provided thereon with an optical system for guiding light from said gel to said photoelectric conversion part.

6. A fluorescence detection type gel electrophotresis apparatus in accordance with claim 1, wherein said scanning mechanism includes a moving stage, and said moving means includes an optical system for deflecting excitation light, said moving means is separated from said moving stage, while said moving stage is provided thereon with an optical system for guiding light from said moving means to said gel.

7. A fluorescence detection type gel electrophoresis apparatus in accordance with claim 1, wherein said moving means comprises a mirror for reflecting excitation light and introducing the same into said gel and a galvano scanner for rotating said mirror.

8. A fluorescence detection type gel electrophoresis apparatus in accordance with claim 1, wherein said moving means comprises a mirror for reflecting excitation light and introducing the same into said gel and a piezoelectric element for moving said mirror in parallel.

9. A fluorescence detection type gel electrophoresis apparatus in accordance with claim 1, wherein said moving means comprises a mirror for reflecting said excitation light and introducing the same into said gel and an acoustic optical element for changing the optical path of said excitation light being introduced into said mirror.

10. A fluorescence detection type gel electrophoresis apparatus in accordance with claim 1, wherein said excitation optical system and said light receiving optical system are so arranged that an angle of incidence of said excitation light with respect to said gel is in a range of 20° to 35°.

11. A fluorescence detection type gel electrophoresis apparatus in accordance with claim 1, wherein a microcomputer is provided in order to control said scanning mechanism and said moving means, and another microcomputer is provided in order to incorporate a measuring signal being received through said light receiving optical system and photoelectrically converted.

* * * * *